United States Patent [19]
Sabesan et al.

[11] Patent Number: 5,276,143
[45] Date of Patent: Jan. 4, 1994

[54] DIDEOXYFRUCTONUCLEOSIDES AND DEOXYFRUCTONUCLEOTIDES

[75] Inventors: Subramaniam Sabesan; George L. Trainor, both of Wilmington, Del.

[73] Assignee: E. I. Du Pont de Nemours and Company, Wilmington, Del.

[21] Appl. No.: 631,567

[22] Filed: Dec. 21, 1990

[51] Int. Cl.$^5$ .................. C07H 19/073; C07H 19/10; C07H 19/14; C07H 19/207
[52] U.S. Cl. .............................. 536/26.23; 536/26.26; 536/26.7; 536/26.74; 536/26.8; 536/26.9; 536/27.14; 536/27.5; 536/28.2
[58] Field of Search .................. 536/23, 24, 26, 27, 536/28, 29, 26.23, 26.26, 26.7, 26.74, 26.8, 26.9, 27.14, 27.5, 28.2

[56] References Cited

U.S. PATENT DOCUMENTS 3,280,104 10/1966 Moffatt et al. .................. 536/28
4,724,232 10/1988 Rideout et al. .................. 514/50

FOREIGN PATENT DOCUMENTS 61-275290 12/1986 Japan .................. 536/26.8

OTHER PUBLICATIONS

Maxam et al., Methods of Enzymology, vol. 65, 499–560 (1980).
Sanger et al., Proc. Nat. Acad. Sci. USA, vol. 74, 5463–5467 (1977).
Prober et al., Science, 238, 336–341 (1987).
Langer et al., Proc. Nat. Acad. Sci. USA, 78, 6633–6637 (1981).
Sturm et al., J. Org. Chem., vol. 47, 4367–4370 (1982).
Tatsuoka et al., Heterocycles, vol. 24, No. 8, 2133–2136 (1986).
Tatsuoka et al., Heterocycles, vol. 24, No. 3, 617–620 (1986).
Mathews & van Holde, *Biochemistry,* Benjamin/Cummings Publishing Co., New York, N.Y., 1990, Ch. 22, particularly pp. 771–777.
Faivre-Buet et al., "Sythesis of 1-deoxypsicofuransyl-deoxynucleosides as Potential Anti-HIV Agents", *Nucleosides Nucleotides,* 11(7), 1411–1424 (1992); *Chem. Abstr.,* 117(19), p. 847, Abstr. No. 192239p, 1992; only Abstract supplied.
Thompson et al., "Intracellular Hexose-6-phosphate: Phosphohydralase from *Streptococcus lactis.* Purification Properties and Function", *J. Bacteriology,* 156(1), 70–80 (1983).
Kaulinya et al., "Analogs of Pyrimidine Nucleosides. 16. Racemic 2′,3′-Dideoxynucleosides and Their Derivatives", translated from *Khimiya Geterotsiklicheskikh Soedinenii,* 1982(1), 101–110.

*Primary Examiner*—John W. Rollins
*Assistant Examiner*—L. Eric Crane

[57] ABSTRACT

Disclosed are deoxyfructonucleotides and dideoxyfructonucleotides which may be used as propagators and terminators in DNA extension reactions.

3 Claims, No Drawings

DIDEOXYFRUCTONUCLEOSIDES AND DEOXYFRUCTONUCLEOTIDES

FIELD OF THE INVENTION

This invention relates to deoxyfructonucleotides and dideoxyfructonucleotides and their use in DNA extension reactions.

BACKGROUND

DNA sequencing is one of the cornerstone analytical techniques of modern molecular biology. The development of reliable methods for sequencing has led to great advances in the understanding of genetic information and has made possible the manipulation of genetic material (i.e., genetic engineering).

There are currently two methods for sequencing DNA: the Maxam-Gilbert chemical degradation method [Maxam et al., Meth. in Enzym., Vol. 65, 499–559 (1980)] and the Sanger dideoxy chain termination method [Sanger et al., Proc. Nat. Acad. Sci. USA, Vol. 74, 5463–5467 (1977)]. A common feature of these two techniques is the generation of a set of DNA fragments which are analyzed by electrophoresis. The techniques differ in the methods used to prepare these fragments.

With Sanger's technique, DNA fragments are produced through partial enzymatic copying (i.e., synthesis) of the piece of DNA to be sequenced. In the most common version, the piece of DNA to be sequenced is inserted, using standard techniques, into a "sequencing vector"; a large, circular, single-stranded piece of DNA such as the bacteriophage M13. This becomes the template for the copying process. A short piece of DNA with its sequence complementary to a region of the template just upstream from the insert is annealed to the template to serve as a primer for the synthesis. In the presence of the four natural deoxyribonucleoside triphosphates (dNTP's), a DNA polymerase will extend the primer from the 3'-end to produce a complementary copy of the template in the region of the insert. To produce a complete set of sequencing fragments, four reactions are run in parallel, each containing the four dNTP's along with a single dideoxyribonucleoside triphosphate (ddNTP) terminator, one for each base. ($^{32}$P-labeled dNTP is added to give labeled fragments). If a dNTP is incorporated by the polymerase, chain extension can continue. If the corresponding ddNTP is selected, the chain is terminated. The ratio of ddNTP to dNTP's is adjusted to generate DNA fragments of appropriate lengths. Each of the four reaction mixtures will, thus, contain a distribution of fragments with the same dideoxynucleotide residue at the 3'-terminus and a primer-defined 5'-terminus.

The key to the success of the Sanger method is the ability of the ddNTP's to function as chain terminating substrates which, after incorporation, prohibit further chain extension. The number of available chain terminating substrates is limited. Novel chain terminating substrates would be useful and valuable because they would expand the utility of the Sanger method.

The present invention relates to the use of dideoxyfructonucleotides as chain terminating substrates and deoxyfructonucleotides as chain propagating substrates in DNA chain extension reactions. Specifically, these novel compounds differ from the deoxynucleotides and dideoxynucleotides generally used in extension or termination reactions in that they possess a functional-group-bearing methylene unit at the anomeric carbon of the sugar residue. This one-carbon extension is a potential site for the attachment of reporters (detectable groups) such as fluorescent dyes or biotin. Reporter-labeled chain terminators have been shown to be useful in non-radioisotopic sequencing. Prober et al., Science, 238, 336–341 (1987). Reporter labeled chain propagators are useful in the labeling and detection of DNA fragments. Langer et al., Proc. Natl. Acad Sci. USA, 78, 6633–6637 (1981). In the compounds provided by the instant invention, the reporter may be contained within the sugar portion rather than the purine or pyrimidine portion of the molecule, as in previously developed methodogy. Hence, since the sugar portion of the nucleotide base is common to all nucleotides, a single fructosugar derivative would provide a convenient and universally useful means by which all nucleotides to be used in nucleotide extension or termination reactions could be prepared via a common intermediate.

References which disclose structurally related compounds include: Sturm et al., J. Org. Chem., Vol. 47, 4367–4370 (1982), which discloses a cyclic 4',6'-monophosphate of psicofuranine; Tatsuoka et al., Heterocycles, Vol. 24, No. 8, 2133–2136 (1986), which discloses synthesis of 1'-deoxy-1'-phosphono-1-β-D-fructofuranosyluracil and 1',3'-dideoxy-1'-phosphono-1-β-D-fructofuranosyluracil; Tatsuoka et al., Heterocycles, Vol. 24, No. 3, 617–620 (1986), which discloses synthesis of 2,3'anhydro-1'-phosphono-1-B-D-fructofuranosyl uracil; and Tatsuoka et al., Japanese Patent 61-275290.

SUMMARY OF THE INVENTION

This invention provides compounds which have utility as terminators in DNA extension reactions and compounds which have utility as propagators in DNA extension reactions. The compounds provided by this invention comprise those of Formula I.

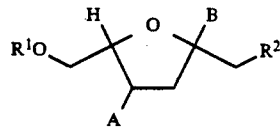

wherein:

R$^1$ is H$_2$PO$_3$, H$_3$P$_2$O$_6$, H$_4$P$_3$O$_9$ and the salts thereof, or H;

B is a naturally occurring nucleic acid base or synthetic modified nucleic acid base;

R$^2$ is OR$^3$, N$_3$, Y-Biotinoyl, or NHC=O(CH$_2$)$_n$Y-Biotinoyl; wherein:

R$^3$ is H, alkyl, aralkyl, acyl or aroyl, wherein:

the alkyl may be of 1 to 5 carbon atoms;

the aralkyl group may be benzyl;

the acyl may be of 1 to 5 carbon atoms;

the aryl group of the aroyl may be benzene, or a benzene substituted with at least one alkyl group (of C$_1$–C$_5$), one halogen atom, or one methoxy group;

Y is NH or O;

n=1–10, and

A is H or OH.

In a preferred form, the compound as recited in Formula I would be provided wherein:

R$^1$ is H$_2$PO$_3$, H$_3$P$_2$O$_6$, H$_4$P$_3$O$_9$ or the salts thereof, or H;

B is a naturally occurring nucleic acid base;

$R^2$ is OH, $N_3$, or Y-Biotinoyl; and
A is H.

In a most preferred form, the compound of Formula I would be provided wherein:
$R^1$ is $H_4P_3O_9$;
B is thymine;
$R^2$ is OH, $N_3$, or Y-Biotinoyl; and
A is H.

This invention also provides nucleic acid chains which may contain any of the compounds of Formula I.

This invention also provides a process for synthesis of a nucleic acid chain wherein the compounds of the invention may be combined with one or more naturally occurring or synthetically modified nucleic acids to form a nucleic acid chain.

This invention also provides a process for terminating DNA polymerase extension reactions comprising addition of a dideoxyfructonucleotide compound of Formula I, (when A is H,) to a DNA polymerase extension reaction.

This invention also provides a process for propagating DNA polymerase extension reactions comprising addition of a deoxyfructonucleotide compound of Formula I, (when A is OH,) to a DNA polymerase extension reaction.

DETAILED DESCRIPTION OF THE INVENTION

The term "nucleoside" is used throughout to denote a heterocyclic base-sugar unit composed of one molecule of pyrimidine or purine and one molecule of a ribose sugar. The term "nucleotide" is used throughout to denote its phosphorylated derivative.

The term "fructonucleoside" is used throughout to denote a heterocyclic base-sugar unit composed of one molecule of pyrimidine or purine and one molecule of a fructose sugar. The term "fructonucleotide" is used throughout to denote its phosphorylated derivative.

The term "naturally occurring nucleic acid base" is used to designate the heterocyclic base attached to the C-1 of each sugar unit in a nucleoside or nucleotide, such as adenine, thymine, cytosine, guanine or uracil.

The term "synthetically modified nucleic acid base" is used to mean a chemically synthesized or naturally occurring nucleic acid base which has been chemically modified, such as inosine or deazaadenosine.

The terms "terminator", "chain terminator" and "chain terminating substrate" are used interchangably throughout to denote a substrate which can be incorporated onto the 3'-end of a DNA chain by an enzyme which replicates nucleic acids in a template-directed manner but, once incorporated, prevents further chain extension. The dideoxyfructonucleotide compounds of the present invention, wherein A is H, exemplify chain terminating substrates. In contrast, the natural deoxynucleotide and analogous synthetically modified deoxynucleotide substrates are considered to be "chain propagating substrates" (or "propagators"), and do not act to terminate further nucleic acid chain formation after their incorporation by the polymerase. The deoxyfructonucleotides of the present invention, wherein A is OH, exemplify chain propagating substrates.

The terms "nucleotide polymerase extension reaction", or "polymerase extension reaction" refer to a method of enzymatically synthesizing specific regions of a nucleic acid molecule, as elaborated in Sanger et al., Pro. Nat Acad. Sci. USA, Vol. 74, 5463–5467 (1977), which is hereby incorporated by reference. The method is based upon techniques wherein an oliogo-nucleotide primer is annealed to a desired site on a template nucleic acid, and in the presence of excess deoxynucleotides a polymerase is used to extend the primer from the 3'-end, thereby producing a complementary copy of the template nucleic acid. The polymerase extension reaction has been further elaborated to provide a means of nucleic acid sequencing by making use of dideoxynucleotides which act as chain terminators. (Sanger et al., supra.)

Compounds of Formula I, (when A is H) which are the claimed dideoxyfructonucleotide compounds, can be prepared from compounds of Formula II (below).

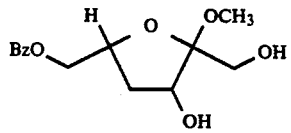

II

A compound of Formula II, which serves as a common intermediate for the preparation of claimed compounds, can be prepared from fructose by a six step process.

In step one, fructose is converted to methyl fructofuranoside by reaction in methanol using sulfuric acid as the catalyst; this reaction yields an anomeric mixture of methyl α,β-fructofuranosides. In step two, the 1- and 3-hydroxyl groups of the product of step one are protected by conversion to a benzylidene derivative. For example, reaction of the described anomeric mixture of methyl α,β-fructofuransides with benzaldehyde dimethylacetal and a proton source such as p-toluenesulfonic acid, yields methyl 1,3-O-benzylidene-α-D-fructofuranoside. In step three, the 6-hydroxy group of the product of step two is protected by conversion to a trialkylsilyl ether. For example, reaction of 1,3-O-benzylidene-α-D-fructofuranoside with t-butyldimethylsilyl chloride and imidazole yields the t-butyldimethylsilyl ether derivative methyl 1,3-O-benzylidene-6-O-t-butyldimethylsilyl-α-D-fructofuranoside. In step four, the 4-hydroxy group of the product of step three is replaced with a hydrogen atom. For example, reaction of 1,3-O-benzylidene-6-O-t-butyldimethylsilyl-α-D-fructofuranoside with thiocarbonyldiimidazole affords an intermediate which is then reacted with tri-n-butyl tin hydride and azo(bis)isobutyronitrile (AIBN) to yield the deoxy derivative, methyl 1,3-O-benzylidene-6-O-t-butyl-dimethylsilyl-4-deoxy-α-D-fructofuranoside. In step five, the trialkylsilyl group is removed from the 6-O-trialkysilyl ether of the product of step four, and the resulting 6-hydroxy group is esterified. For example, reaction of methyl 1,3-O-benzylidene-6-O-t-butyl-dimethylsilyl-4-deoxy-α-D-fructofuranoside with tetrabutylammonium fluoride affords the 6-hydroxy derivative, methyl 1,3-O-benzylidene-4-deoxy-α-D-fructofuranoside which is then reacted with benzoyl chloride to give the O-ester derivative, methyl 6-O-benzoyl-1,3-O-benzylidene-4-deoxy-α-D-fructofuranoside.

Compounds of Formula II, which serve as intermediates to compounds of Formula I (when A is H), are produced in step six in which the 1,3-O-benzylidene group is removed giving a derivative with 1,3-dihydroxy groups. For example, reaction of 6-O-benzoyl-1,3-O-benzylidene-4-deoxy-α-D-fructofuranoside in an acidic medium such as an alcohol containing p-toluenesulfonic acid yields the methyl 6-O-benzoyl-4-deoxy- α,β-D-fructofuranoside. The α anomer, methyl 6-O-benzoyl-4-deoxy-α-D-fructofuranoside, and β anomer, methyl 6-O-benzoyl-4-deoxy-β-D-fructofuranoside, of the anomeric mixture obtained in step six may then be separated from each other and isolated in anomerically pure form by chromatography.

Compounds of Formula I (when A is H) can be synthesized from compounds of Formula II by performing a series of reactions on compounds of Formula II. For example, 1-N-(3,4-dideoxy-D-glycero-β-D-hex-2-ulofuranosyl) thymine can be prepared from methyl 6-O-benzoyl-4-deoxy-α,β-D-fructofuranoside in four steps. In step one of this reaction sequence, methyl 6-O-benzoyl-4-deoxy-α,β-D-fructofuranoside is reacted with a benzoyl halide in the presence of a mild base to give the 1,6-di-O-benzoyl derivative, methyl 4-deoxy-1,6-di-O-benzoyl-α,β-D-fructofuranoside. In step two, the 3-position of the product of step one is deoxygenated to give methyl 1,6-di-O-benzoyl-3,4-dideoxy-α,β-D-fructofuranoside by reaction of the product of the first step with 1,1'-thiocarbonyl diimidazole and tri-n-butyltin hydride; furthermore, the anomers are separated from each other and purified by chromatography. In step three, the β-anomer from step two is converted to the dideoxy-fructonucleoside derivative, 1-N-(1,6-Di-O-3,4-dideoxy-D-glycero-β-D-hex-2-ulofuranosyl) thymine, by reaction with 2,4-di-O-trimethylsilyl thymine. In step four, the 1,6-di-O-benzoyl groups are removed from the product of step three to give the 1,6-dihydroxy derivative, 1-N-(3,4-dideoxy-D-glycero-β-D-hex-2-ulofuranosyl)thymine, by reaction of the product of step three using Zemplen's procedure, A. Thompson, M. L. Wolfrom, Methods In Carbohydrate Chemistry, R. L. Whistler and M. L. Wolfrom Eds.; Associated Press, 1963, vol. II, p215, herein incorporated by reference.

In another example of the preparation of a compound of Formula I (when A is H) from a compound of Formula II, the dideoxy-fructonucleoside derivative, 1-N-(1-azido-1,3,4-trideoxy-D-glycero-β-D-hex-2-ulofuranosyl) thymine was prepared in five steps from methyl 6-O-benzoyl-4-deoxy-β-D-fructofuranoside. In step one, methyl 6-O-benzoyl-4-deoxy-α,β-D-fructofuranoside is reacted with t-butyl-dimethylsilyl halide and imidazole to give the 1-O-t-butyldimethylsilyl ether derivative, methyl 6-O-benzoyl-1-O-t-butyldimethylsilyl-4-deoxy-β-D-fructofuranoside. In step two, the product of the reaction of step one is converted to the 3-deoxygenated product, methyl 6-O-benzoyl-1-O-t-butyldimethylsilyl-3,4-dideoxy-β-D-fructofuranoside, by reaction with thiocarbonyldiimidazole, followed by reaction with AIBN and tri-n-butyltin hydride. In step three, the product of step two is converted to the 1-azido derivative, methyl 1-azido-6-O-benzoyl-1,3,4-trideoxy-β-D-fructofuranoside, by reaction with tetrabutylammonium fluoride to remove the t-butyldimethylsilyl protecting group, followed by reaction with sulfuryl halide and imidazole to give the imidazolide, followed by reaction with sodium azide to give the 1-azido derivative. In step four, the product of step three is converted to the fructonucleoside derivative, 1-N-(1-azido-6-O-benzoyl-3,4-trideoxy-D-glycero-β-D-hex-2-ulofuranosyl) thymine by reaction with 2,4-di-O-trimethylsilylthymine. In step five, the product of step four is converted to the 6-hydroxy fructonucleoside derivative, 1-N-(1-azido-4-trideoxy-D-glycero-β-D-hex-2-ulofuranosyl) thymine, by reaction with sodium methoxide in methanol to remove the benzoyl group.

Compounds of Formula I (where A=OH) are prepared from a starting material such as methyl 1,3-O-benzylidene-α-D-fructofuranoside, described above. In Step 1, the unprotected hydroxy groups of the starting material are protected. For example, reaction of this starting material with an acid halide such as benzoyl chloride and a catalytic amount of a hindered base such a 4-N,N-dimethylaminopyridine in a chlorinated solvent such as methylene chloride containing pyridine gives methyl 1,3-O-benzylidene-4,6-di-O-benzoyl-α-D-fructofuranoside. In Step 2, the protecting group is removed the 1,3-hydroxy groups and the 1-hydroxy group is protected with another protecting group while the 3-hydroxy group remains unprotected. For example, reaction of the product of Step 1 with an acid catalyst such as p-toluene sulfonic acid in refluxing anhydrous methanol removes the benzylidene protecting group. Next, reaction of the resulting dihydroxy compound with imidazole and a trialkysilyl halide such as t-butyldimethylsilyl chloride in a polar aprotic solvent such as dimethyl formamide gives methyl 4,6-di-O-benzoyl-1-O-(t-butyldimethyl)silyl-α,β-D-fructofuranoside. Finally, the α and β anomers generated by the reaction of Step 2 are separated by chromatography. In Step 3, one of the anomers of Step 2 is converted to the 3-deoxy derivative. For example, reaction of 4,6-di-O-benzoyl-1-O-(t-butyldimethyl)silyl-β-D-fructofuranoside with thiocarbonyldiimidazole in a chlorinated solvent such as 1,2-dichloroethane affords an intermediate which is then reacted with tri-n-butyl tin hydride in a hydrocarbon solvent such as toluene gives methyl 3-deoxy-4,6-di-O-benzoyl-1-O-(t-butyldimethyl)silyl-β-D-fructofuranoside. In Step 4, the product of Step 3 is converted to the 1-azido derivative, methyl 1-azido-1,3-dideoxy-4,6-di-O-benzoyl-β-D-fructofuranoside, by reaction of it with tetrabutylammonium fluoride to remove the t-butyldimethylsilyl protecting group, followed by reaction with sulfuryl chloride and imidazole to give the imidazolide, followed by reaction with sodium azide in anhydrous dimethylformamide. In Step 5, the product of Step 4 would be converted to 1-N-(1-azido-3,6-dibenzoyl-1,3-dideoxy-D-erythro-β-D-hex-2-ulo)furanosyl)thymine by reaction of it with 2,4-di-O-trimethylsilylthymine. In Step 6, the product of Step 5 would be converted to the final product, 1-N-(1-azido-1,3-dideoxy-D-erythro-β-D-hex- 2-ulofuranosyl)thymine by reaction of it with sodium methoxide in methanol.

Compounds of Formula I where $R^1$ is $H_4P_3O_9$ are prepared from compounds of Formula I where $R^1$ is H. For example, 1-N-(3,4-dideoxy-D-glycero-β-D-hex-2-ulofuranosyl)thymine 6-triphosphate is prepared by adding phosphorous oxychloride to a suspension of 1-N-(3,4-dideoxy-D-glycero-β-D-2-ulofuranosyl)thymine and cytosine in trimethyl phosphate and stirring the resultant mixture, under Argon, for forty minutes, followed by addition of the resultant mixture to a solution of tris(tri-n-butylammonium) pyrophosphate in dimethylformamide.

The present invention also comprises a nucleic acid chain of at least two nucleic acid bases in length, wherein one or more of these nucleic acid bases is a compound of Formula I.

The invention also provides a process for synthesis of such nucleic acid chains, wherein during DNA synthesis reactions, one or more of the compounds of Formula I is supplied in the reaction mixture for incorporation into a nucleic acid chain. Such nucleic acid chains can be prepared for example, by combining one or more of the compounds of Formula I with one or more discreet naturally occurring or synthetically modified nucleic acid bases using any of the standard methods, which are well known in the art, for oligonucleotide synthesis.

The present invention further comprises a process for terminating DNA polymerase extension reactions comprising addition to a DNA polymerase extension reaction mixture one or more of the compounds of Formula I when A is H: in other words, when the compound of Formula I exists in the dideoxy form.

If the dideoxynucleotide is incorporated by a DNA polymerase in a DNA chain extension reaction, chain extension will not continue and the extension is terminated. The Sanger method of DNA sequencing relies upon dideoxy chain termination to generate a series of nucleic acid fragments which are then analyzed to reveal DNA sequence. See Sanger et al., Proc. Nat. Acad. Sci. USA, Vol. 74, 5463-5467 (1977) which is hereby incorporated by reference.

The present invention further comprises a process for propagating DNA polymerase extension reactions comprising addition to a DNA polymerase extension reaction mixture one or more of the compounds of Formula I when A is OH: in other words, when the compound of Formula I exists in the deoxy form. Deoxynucleotides will allow chain extension to continue after incorporation into a nucleic acid chain during a polymerase chain extension reaction. (Sanger et al., supra).

EXAMPLES

Example 1

Synthesis of a Compound of Formula I where $R^1$ is H, $R^2$ is $OR^3$, $R^3$ is H, B is thymine and A is H; 1-N-(3,4-dideoxy-D-glycero-$\beta$-D-hex-2-ulofuranosyl) thymine

Step 1: (Methyl $\alpha,\beta$-fructofuranosides)

For the preparation of this compound the procedure followed was that of R. D. Guthrie et al., J. Chem. Soc. Perkin 1, 46, 4843 (1981). To a suspension of 100 g of fructose in anhydrous methanol (1L), 15 mL of conc. sulfuric acid was added in drops and stirred at room temperature for 30 min. The solution was then neutralized with AG1-X8 (OH form) resin and then filtered. The solution was then evaporated to dryness. The product contained a mixture of methyl $\alpha,\beta$-fructofuranosides and minor amounts of pyranoside and traces of unreacted fructose. This mixture was used in subsequent reactions.

Step 2: (Methyl 1,3-O-benzylidene-$\alpha$-D-fructofuranoside)

The anomeric mixture of methyl fructoside syrup from Step 1 was dissolved in anhydrous methanol containing 4 Å molecular sieves and left overnight. The solution was then filtered and evaporated to a syrup which was left under high vacuum to remove the residual solvent. This was then suspended in 700 mL of anhydrous acetonitrile. A solution of acetonitrile (348 mL) containing benzaldehyde dimethylacetal (87 mL) and p-toluenesulfonic acid (1.00 g) was added in drops to the above methyl fructoside suspension maintained at 60° C. with vigorous stirring for 24 h and then at room temperature for 24 h. The solution was then neutralized with triethylamine and evaporated to dryness. The desired product from this was separated by chromatography on a column of silica gel using ethyl acetate-hexane-ethanol as eluant (10:10:1). Yield 44.27 g. $^1$H NMR d (CDCl$_3$+D$_2$O ca. 1%): 7.55-7.3 (m, 5H, C$_6$H$_5$), 5.49 (s, 1H, acetal CH), 4.45 (H-1a, 1H, $J_{1a,1b}$=11.7 Hz), 4.23 (m, 1H, H-5), 4.19 (s, 1H, H-3), 4.09 (d, 1H, H-4, $J_{4,5}$=2.5 Hz), 3.98 (d, 1H, H-1$_b$), 3.85 (m, 2H, H-6$_{a,b}$). $^{13}$C NMR d: 136.7, 129.4, 128.4, 126.0 (C$_6$H$_5$), 100.5 (C-2), 100.0 ( benzylic acetal carbon), 88. 9 (C-3), 84.6 (C-5), 77.0 (C-4), 68.0 (C-1), 62.9 (C-6), 49.1 (OCH$_3$).

The compound was contaminated with products that had almost identical mobility when examined by silica gel thin layer chromatography. However, these could be easily removed by converting the product to the t-butyldimethylsilyl derivative as described below.

Step 3: (Methyl 1.3-O-benzylidene-6-O-t-butvldimethylsilyl-$\alpha$-D-fructofuranoside)

The product from Step 2 (44.27 g) was dissolved in anhydrous dimethyformamide (250 mL) containing imidazole (12.1 g) and cooled to 0° C. A solution of t-butyldimethylsilylchloride (24.2 g) in DMF (50 mL) was added slowly, and the solution was stirred for 2 h. The solvent was then evaporated under vacuum and dissolved in dichloromethane. The dichloromethane layer was washed with water, ice-cold 1 M hydrochloric acid, and then saturated sodium bicarbonate solution. The desired product was obtained by purification on a column of silica gel using ethylacetate-hexane (3:8) as eluant. Weight of pure product 29.4 g. Slightly (<10%) impure product 10.2 g. $^1$H nmr (CDCl$_3$) d: 7.35-7.5 (m, 5H, C$_6$H$_5$), 5.45 (s, 1H, PhCH), 4.4 (d, 1H, H-1a, $J_{1a,1b}$=12.0 Hz), 4.16 (m, 2H, H-5, H-3), 4.07 (d, 1H, H-4, $J_{4-OH}$=11.0 Hz), 3.97 (d, 1H, H-1$_b$), 3.87 (dd, 1H, H-6a, J 5,6=6.0 Hz, J $_{6a,6b}$=10.6 Hz), 3.76 (dd, 1H, H-6$_b$, J$_{5,6b}$=8 Hz), 3.37 (s, 3H, OCH$_3$), 2.66 (d, 1H, OH), 0.88 (s, 9H, C$_4$H$_9$-Si), 0.08 (broad s, 6H, 2×CH$_3$ -Si). $^{13}$C NMR d: 137.1, 129.1, 128.2, 126.1 (C$_6$H$_5$), 100.5 (C-1), 99.8 (Benzylic acetal carbon), 89.1 (C-3), 84.5 (C-5), 77.53 (C-4), 68.0 (C-1), 64.0 (C-6), 48.9 (OCH$_3$), 25.9 (CH$_3$)$_3$), 18.3 {(CH$_3$)$_3$-C), -5.3, -5.2 (2×CH$_3$).

Step 4: (Methyl 1,3-O-benzylidene-6-O-t-butyldimethylsily-4-deoxy-$\alpha$-D-fructofuranoside A solution of the product of Step 3 (5.6 g) in anhydrous 1,2-dichloroethane (100 mL) containing thiocarbonyldiimidazole (6.8 g) was refluxed for a period of 16 h under nitrogen atmosphere. The solution was then cooled and diluted with dichloromethane. The organic layer was washed with water, ice cold 0.5M hydrochloric acid and the with saturated sodium bicarbonate solution. Evaporation of solvent after drying over anhydrous magnesium sulfate afforded a foam, which was coevaporated twice with anhydrous toluene and then dissolved in anhydrous toluene (200 mL). The solution was degassed with dry nitrogen for 30 min. AIBN (vazo 64, 25 mg) was then added and the solution was refluxed while adding solutions of tri-n-butyl tin hydride (4.5 mL) in toluene (21.5 mL) and AIBN (60 mg) in toluene (25 mL). After the addition was completed over a period of 1 h, the solution was refluxed for another 30 min. by which time all the starting material had disappeared. The solution was cooled and then washed with water, 10% aq.potassium fluoride solution, ice cold 0.5M hydrochloric acid and then with sat. sodium bicarbonate solution. Evaporation afforded a colorless oil from which the desired product was obtained by chromatography on a column of silica gel equilibrated and eluted with ethyl acetate-hexane (1:8). Yield of the syrup 4.0 g. $^1$H NMR (CDCl$_3$) d: 7.5–7.34 (m, 5 H, C$_6$H$_5$), 5.44 (s, 1H, PhCH), 4.41 (d, 1 H, H-1a, J$_{1a,b}$=12.5 Hz), 4.27 (m, 1H, H-5), 4.19 (d, 1 H, H-3, J$_{3,4a}$=5.8 Hz), 3.93 (d, 1H, H-1$_b$), 3.92 (dd, 1 H, H-6a, J$_{a,b}$=11.6 Hz, J$_{6a,5}$=6.5 Hz), 3.72 (dd, 1 H, H-6b, J$_{6b,5}$=8.7 Hz), 3.29 (s, 3H, OCH$_3$), 2.44 (m, 1 H, H-4a, J$_{4a,3}$=5.8 Hz, J$_{4a,5}$=9.6 Hz, J$_{4a,b}$=14.5 Hz), 1.90 (dd, 1 H, H-4b, J$_{4b,5}$=3.8 Hz), 0.90 {s, 9 H, (CH$_3$)$_3$-C}, 0.07 (broad s, 6 H, 2×CH$_3$). $^{13}$C NMR d: 137.7, 129.0, 128.2, 126.2 (C$_6$H$_5$), 100.2 (C-2), 100.0 (PhCH), 80.3 (C-3), 79.8 (C-5), 69.9 (C-1), 66.7 (C-6), 48.7 (OMe), 33.2 (C-4), 25.9 (3×CH$_3$ of t-butyl group), 18.4 {(CH$_3$)$_3$-C), -5.1, −5.3 {2×(CH$_3$)$_2$-Si}.

Step 5: (Methyl 6-O-benzoyl-1,3-O-benzylidene-4-deoxy-α-D-fructofuranoside)

To a solution of the product of Step 4 (6.4 g) in anhydrous tetrahydrofuran (THF, 100 mL), 1M tetrabutylammonium fluoride solution (23 mL) in THF was added and stirred at room temperature for 1.5 h. The solution was then evaporated to dryness, redissolved in dicloromethane and then washed with water, 0.5M HCl and sat. NaHCO$_3$ solution. After evaporation, the residue was taken up in anhydrous pyridine (50 mL) and cooled to 0° C. Benzoyl chloride (4.2 mL) was added and the reaction mixture was warmed up to room temperature and stirred for 16 h. The solution was then poured over ice, and the product was extracted with dichloromethane. The organic layer was then washed with 1M HCl and aqueous sat. NaHCO$_3$ solution. The residue obtained after evaporation was purified by filtration on a column of silica gel equilibrated and eluted with ethylacetate-hexane (1:6). The yield of the colorless solid was 5.63 g. The sample was recrystallized from ethyl acetate-hexane to get colorless needles. $^1$H NMR (CDCl$_3$) d: 8.0, 7.5, 7.37 (m, 5 H, C$_6$H$_5$), 5.49 (s, 1 H, PhCH), 4.45–4.62 (m, 4H, H-5, H-6a,b H-1a), 4.26 (d, 1 H, H-3, J$_{3,4a}$=5.0 Hz), 3.97 (d, 1 H, H-1$_b$, J$_{1a,b}$=Hz), 3.32 (s, OMe), 2.57 (m, 1H, H-4a, J$_{4a,3}$=5.0 Hz, J$_{4a,5}$=8.5 Hz, J$_{4a,b}$=14.2 Hz), 1.99 (dd, 1 H, H-4b, J$_{4b,5}$=2.8 Hz).

Step 6: (The compound of Formula II. methyl 6-O-benzoyl-4-deoxy-α,β-D-fructofuranoside)

A solution of the product of Step 5 (5.6 g) in anhydrous methanol (140 mL) containing p-toluenesulfonic acid (374 mg) was refluxed for 30 min. The reaction mixture was cooled and neutralized with triethylamine. The solution was evaporated to dryness and applied on a column of silica gel equilibrated and eluted with etylacetate-ethanolhexane (10:1:10). Two fractions were obtained, methyl 6-O-benzoyl-4-deoxy-α-D-fructofuranoside and methyl 6-O-benzoyl-4-deoxy-β-D-fructofuranoside; methyl 6 -O-benzoyl-4-deoxy-β-D-fructofuranoside was the more polar of the two. The yield of methyl 6-O-benzoyl-4-deoxy-α-D-fructofuranoside was 2.45 g (syrup). The yield of methyl 6-O-benzoyl-4-deoxy-β-D-fructofuranoside was 1.47 g. The structures of methyl 6-O-benzoyl-4-deoxy-α-D-fructofuranoside and methyl 6-O-benzoyl-4-deoxy-β-D-fructofuranoside were established by $^1$H and $^{13}$C nmr.

$^1$H NMR (CDCl$_3$+D$_2$O ca. 1%) d (α anomer): 8.05, 7.59, 7.47 (d, 2 H, t, 1 H, t, 2 H respectively, ortho, meta and para hydrogens of C$_6$H$_5$), 4.52 (dd, 1 H, H-6a), 4.45 (m, 1 H, H-5), 4.35 (dd, 1 H, H-6b), 4.25 (dd, 1H, H-3), 3.85 (t, 2 H, H-1a,b), 3.35 (s, 3 H, OMe), 2.55 (m, 1H, H-4β), 2.78 (m, 1H, H-4a). $^{13}$C NMR (CDCl$_3$) d: 166.6 (COPh), 133.1, 129.6, 128.4 (C$_6$H$_5$CO), 109.1 (C-2), 76.5 (2×C, C-5, C-3), 66.7 (C-6), 58.9 (C-1), 48.7 (OMe), 35.5 (C-4).

$^1$H NMR (CDCl$_3$+D$_2$O ca. 1%) d (β anomer): 8.08, 7.57, 7.46 (d 2 H, t , 1 H, & t, 2 H, respectively, ortho, meta and para hydrogens of the benzoate), 4.35 (m, 4 H, H-5, H-3, H-6a,b), 3.70 (dd, 2H, H-1a,b), 3.34 (s, 3 H, OMe), 2.41 (m, 1 H, H-4β), 1.82 (m, 1 H, H-4a). $^{13}$C NMR (CDCl$_3$) d: 166.4 (COPh), 133.1, 129.6, 128.4 (C$_6$H$_5$), 103.3 (C-2), 74.9 (C-5), 73.5 (C-3), 66.9 (C-6), 60.4 (C-1), 49.1 (OMe), 34.2 (C-4).

Step 7: (Methyl 4-deoxy-1.6-di-O-benzoyl-α,β-D-fructofuranoside)

To about 1 g of crude methyl 6-O-benzoyl-4-deoxy-α,β-D-fructofuranoside (prepared as described in Example 1, Step 6) in dichloromethane (25 mL) containing 4 Å molecular sieves and pyridine (0.28 mL) and maintained at −40° C., benzoyl chloride (0.4 mL) was added and the solution was stirred between −30° to −20° C. for 5 h. The reaction mixture was filtered, diluted with dichloromethane and washed with ice cold 0.5M HCl, sat. aqueous NaHCO$_3$ solution, dried over magnesium sulfate and evaporated. Final purification was effected by chromatography on a column of silica gel. The yields of the separated anomers were 0.582 g of methyl 4-deoxy-1,6-di-O-benzoyl-α-D-fructofuranoside and 0.200 g of methyl 4-deoxy-1,6-di-O-benzoyl-β-D-fructofuranoside.

$^1$H NMR (CDCl$_3$) d (α anomer): 8.07 (m, 4 H), 7.58 (m, 2 H), 7.45 (m, 4 H) (ortho, meta and para hydrogens of the 1 and 6-O-benzoates), 4.77 (d, 1 H, H-1a, J$_{1a,1b}$=Hz), 4.51 (d, 1 H, H-1$_b$), 4.44 (m, 3 H. H-5, H-6a,b), 4.05 ( broad triplet collapses to a doublet on D$_2$O exchange, 1 H, H-3, J$_{3,4}$=5.5 Hz), 3.68 (dd, 1 H, OH-3, J=4.2, 1.5 Hz), 3.35 (s, 3 H, OMe), 2.59 (m, 1H, H-4$_a$), 1.88 (dd, 1 H, H-4β).

β-Anomer (CDCl$_3$) d: 8.06 (m, 4 H), 7.57 (m, 2 H) & 7.45 (m, 4 H) ortho, meta and para hydrogens of 1 and 6-O-benzoates, respectively), 4.52 and 4.47 (H-1a & H-1b, J=11.8 Hz), 4.48–4.32 (4 H, H-5, H-6a and H-6b, H-3), 3.45 (s, 3 H, OMe), 2.57 (d, 1 H, 3-OH, J=9.7 Hz), 2.47 (m, 1 H, H-4a, J=6.3, 7.3, 12.2 Hz), 1.97 (m, 1 H, H-4β, J=9.9.6, 12.2 Hz).

Step 8A: (Methyl 1.6-di-O-benzoyl-3.4-dideoxy-α-D-fructofuranoside)

A solution of 574 mg of methyl 4-deoxy-1,6-di-O-benzoyl-α-D-fructofuranoside (from Step 1) in dry toluene (25 mL) containing 1,1'-thiocarbonyl diimidazole (843 mg) was refluxed till all the starting material disappeared (1 to 2 days). The reaction mixture was worked up, and the product was deoxygenated with tri-n-butyltin hydride (0.48 mL) as described for the preparation of methyl 1,3-O-benzylidene-6-O-t-butyldimethylsilyl-4-deoxy-α-D-fructofuranoside in Example 1, Step 4. Purification by chromatography on a column of silica gel (ethyl acetate-hexane=2:9) afforded pure product (265 mg) and slightly contaminated product (53 mg).

Step 8B: (Methyl 1,6-di-O-benzoyl-3,4-dideoxy-β-D-fructofuranoside)

This was prepared from 2.24 g of methyl 4-deoxy-6-di-O-benzoyl-β-D-fructofuranoside (from Step 1) as described in Step 8A. The yield of product was 1.1 g pure and 339 mg of slightly impure product.

Step 9:
(1-N-(1,6-Di-O-benzoyl-3,4-dideoxy-D-glycero-α,β-D-hex-2-ulofuranosyl) thymine)

The dideoxyglycoside from Step 8A (505 mg, 1.36 mmol) and 2,4-di-O-trimethylsilyl thymine (1.09 g, 4.03 mmol) were dissolved in a mixture of nitromethane-dichloromethane (2:1, 11.5 mL) containing 4 Å molecular sieves, stirred at room temperature for 30 min. and then cooled to −30° C. Trimethylsilyl triflate (0.86 mL, 4.43 mmol) was added and the reaction mixture was maintained at −5° C. for 3 h. Triethylamine (2 mL) and dichloromethane (50 mL) were added, and the solution was filtered through a pad of Celite, and the filtrate was washed with water, 0.5M HCl and aqueous bicarbonate solution. The α and the β anomers were separated by HPLC on a column of silica gel using ethyl acetate-hexane-acetonitrile (25:25:4) as the eluant. Yield βanomer, (1-N-(1,6-Di-O-benzoyl-3,4-dideoxy-D-glycero-β-D-hex-2-ulofuranosyl) thymine)=137 mg; yield of the alpha anomer (1-N-(1,6-Di-O-benzoyl-3,4-dideoxy-D-glycero-α-D-hex-2-ulofuranosyl) thymine)=137 mg. $^1$H NMR (β anomer) (CD$_3$COCD$_3$), d: 9.95 (broad singlet, 1 H, N-3H), 7.97, 7.63 and 7.49 (m, total 10 H, 1', 6'-O-benzoate hydrogens), 7.87 (quartet, 1 H, H-6), 4.81 (d, 1 H, H-1'a, $J_{1'a,b}$=11.3 Hz), 4.78 (m, 1 H, H-5'), 4.63 (m, 2H, H-6'a, H-1'b), 4.48 (dd, 1 H, H-6'b, $J_{6'b,5'}$=4.8 Hz, $J_{6'b,6'a}$=12.1 Hz), 3.11 (m, 1H, H-3'β, J=4.6, 7.9, 14.2 Hz), 2.60 (sextet, 1 H, H-3'a, J=8.4, 14.2 Hz), 2.33 and 2.16 (m, 2 H, hydrogens at C-4'), 1.58 (d, 3 H, C-5 Me).

$^1$H NMR (α anomer) (CD$_3$COCD$_3$) d: 10.04 (broad singlet, 1H, N-3H), 8.04, 7.95, 7.64 and 7.48 (m, 10H, 1',6'-O-benzoates), 7.82 (quartet, 1H, H-6), 4.90 (d, 1H, H-1'a, $J_{1'a,b}$=11.2 Hz), 4.68 (m, 1H, H-5'), 4 64 (d, 1H, H-1'b), 4.55 (dd, 1H, H-6'a, $J_{6'a,5'}$=3.8 Hz, $J_{6'a,b}$=11.3 Hz), 4.45 (dd, 1H, H-6'b, $J_{6'b,5'}$=5.5 Hz), 2.94 (septet, 1H, H-3'a, J=6.3, 7.8, 13.8 Hz), 2.65 (octet, 1H, H-3'β, J=6.7, 8.4, 13.8 Hz), 2.25 and 2.13 (m, 2H, H-4 α and β), 1.82 (d, 3H, C-5 Me). $^{13}$C NMR (acetone-d6)) d: 166.5, 166.0, 152.6, 151.4, 136.8, 134.1, 134.0, 130.2, 129.4, 109.5, 99.9 (C-2'), 79.8 (C-5'), 66.6, 66.3 (C-6' and C-1'), 35.0 (C-3'), 27.5 (C-4'), 12.6, 0.0.

Step 10:
(1-N-(3,4-Dideoxy-D-glycero-β-D-hex-2-ulofuranosyl) thymine)

This was prepared quantitatively from 136 mg of the dibenzoate, (1-N-(1,6-Di-O-benzoyl-3,4-dideoxy-D-glycero-β-D-hex-2ulofuranosyl) thymine of Step 9) by Zemplen's procedure (Thompson et al., Methods Carbohydrate Chem., 1962, II, 215) using sodium methoxide in methanol to give a colorless solid (70 mg). $^1$H NMR (D$_2$O) d: 7.98 (broad s, 1H, H-5), 4.34 (m, 1H, H-5'), 3.97 (d, 1H, H-1'a), 3.71 (m, 2H, H-1'b, H-6'a), 3.58 (dd, 1H, H-6'b), 2.68 (m, 1H, H-3'β), 2.25 (m, 1H, H-3'a), 2.02 (m, 1H, H-4'a), 1.84 (broad s, 3H, C-5 Me), 1.65 (m, 1H, H-4'β).

EXAMPLE 2

Synthesis of a Compound of Formula 1 where R$^1$ is H, R$^2$ is N$_3$, B is thymine and A is H; 1-N-(1-Azido-1,3,4-trideoxy-D-glycero-β-D-hex-2-ulofuranosyl) thymine

Step 1A: (Methyl 6-O-benzoyl-1-O-t-butyldimethyl-silyl-4-deoxy-α-D-fructofuranoside)

To a solution of 2.4 g of methyl 6-O-benzoyl-4-deoxy-α-D-fructofuranoside (from Example 1, Step 6) in anhydrous dimethylformamide (20 mL), a solution of t-butyldimethylsilyl chloride (1.40 g) in DMF (5 mL) and imidazole (517 mg) were added and stirred at 0° C. for 3.5 hours. The solution was then evaporated to dryness and the residue was dissolved in dichloromethane. It was washed with water, ice cold HCl, and saturated aqueous sodium bicarbonate solution, dried over anhydrous magnesium sulfate and evaporated. Purification on a column of silica gel afforded 2.6 grams of the title compound as a syrup. (90 mg of the starting material was recovered). $^1$H NMR (CDCl$_3$) d: 8.06, 7.55, and 7.43 (5 H of 6-O-benzoates), 4.420 and 4.25 (4H, H-6a,b, H-5, H-3), 3.95 (d, 1H, H-1a, J=11.4 Hz), 3.84 (d, 1H, H-1$_b$), 3.23 (s, 3H, OMe), 2.49 and 1.76 (m, 2H, H-4a,b), 0.89, 0.09, 0.08 (s 9H).

Step 1B: (Methyl 6-O-benzoyl-1-O-t-butvldimethylsilyl-4-deoxy-β-D-fructofuranoside)

This was prepared from 1.47 g of methyl 6-O-benzoyl-4-deoxy-β-D-fructofuranoside by the same procedure described in Step 1A. Yield 1.37 g. $^1$H NMR βanomer (CDCl$_3$) d: 8.06 (d, 1H, 2H), 7.58 (t, 1H), 7.46 (t, 2H) (ortho, meta and para hydrogens of 6-O-benzoate), 4.35 ( m, 4H, H-5, H-3, H-6a,b), 3.77 (d, 1H, H-1a, $J_{1a,b}$=11.0 Hz), 3.66 (d, 1H, H-1$_b$), 3.33 (s, 3H, OMe), 2.53 (d, 1H, 3-OH, J=8.4 Hz), 2.38 (m, 1H, H-4a), 1.91 (m, 1H, H-4β), 0.91 {s, 9H, (Me)$_3$-}, 0.08 {s, 6H, (Me)$_2$-Si}.

Step 2A: (Methyl 6-O-benzoyl-1-O-t-butyldimethyl-silyl-3,4-dideoxy-α-D-fructofuranoside)

A solution of 3.8 g of the compound of Step 1A and thiocarbonyldiimidazole (7.0 g) in 1,2-dichloroethane (75 mL) was refluxed for 3 days and then worked up and deoxygenated as described above, Step 8A, Example 1. Yield of product was 1.2 g. $^1$H NMR (CDCl$_3$) d: 8.05 (dm, 2H), 7.56 (m, 1H), & 7.44 (m, 1H, 2H) (6-O-benzoate hydrogens), 4.48 (m, 1H, H-5), 4.36 (dd, 1H, H-6a, $J_{6a,5}$=Hz, $J_{6a,b}$=Hz), 4.27 (dd, 1H, H-6b, $J_{6b,5}$=Hz), 3.75 (d, 1H, H-1a, $J_{1a,b}$=11.0 Hz), 3.57 (d, 1H, H-1$_b$), 3.28 (s, 3 H. OMe), 2.17 (m, 2H, H-3a, H-4a), 1.95 (m, 1H, H-3β), 1.70 (m, 1H, H-4β), 0.90 (s, 9H, (Me)$_3$-}, 0.06 (2×s, 6H, (Me)$_2$-Si}.

Step 2B: (Methyl 6-O-benzoyl-1-O-t-butyl dimethylsilyl-3,4-dideoxy-β-D-fructofuranoside)

This was prepared from 2.6 g of the compound of Step 1B. Using the procedure described in Step 2A, the yield of product was 1.5 g.

Step 3A: (Methyl 1-azido-6-O-benzoyl-1,3,4-trideoxy-α-D-fructofuranoside)

A solution of 860 mg of the dideoxy derivative from Step 2A in dry tetrahydrofuran (20 mL) was treated with 1M tetrabutyl ammonium fluoride solution in THF (2.4 mL) and stirred at room temperature for 40 min. The solvent was then evaporated, the residue was dissolved in dichloromethane, washed with water and saturated sodium bicarbonate solution and the solvent was evaporated to get a syrup. This was dissolved in dry DMF (20 mL) containing imidazole (1.47 g) and cooled to −20° C. Sulfuryl chloride (0.452 mL) was added and after 30 min, the solution was brought up to room temperature and stirred for 4 h. The solution was evaporated to dryness, dissolved in dichloromethane and washed with water, ice cold 1M HCl and sodium bicarbonate solution. The residue obtained after evaporation of solvent was dissolved in dry DMF (20 mL) containing sodium azide (300 mg) and heated to 70° C. for 1 h and then at 60° C. for 16 h. DMF was then evaporated and the residue was worked up. Final purification on a column of silica gel (ethyl acetate-hexane=1:6 as eluant) afforded the title compound as a colorless syrup (358 mg). The presence of the azide group was identified by infra red spectrum (strong band at 2108 cm$^{-1}$). The complete structure of the product was confirmed by 1H nmr. $^1$H NMR (CDCl$_3$) d: 8.05 (m, 2H), 7.57 (m, 2H), 7.45 (m, 2 H) (o, m, para hydrogens of the 6-benzoate), 4.51 (m, 1 H, H-5), 4.43 (dd, 1H, H-6a, $J_{6a,5}$=3.3 Hz, $J_{6a,b}$=11.9 Hz), 4.33 (dd, 1H, H-6b, $J_{6b,5}$=5.7 Hz), 3.40 & 3.34 (2×distorted doublets, 2H, H-1a, H-1b, $J_{1a,b}$=12.4 Hz), 3.30 (s, 3H, OMe), 2.27, 2.14, 2.04 & 1.88 (m, hydrogens at C-3 and C-4).

Step 3B: (Methyl 1-azido-6-O-benzoyl-1,3,4-trideoxy-β-D-fructofuranoside)

542 mg of the product of Step 2B was dissolved in THF (20 mL) followed by the addition of 1M solution of tetrabutylammonium fluoride (1.5 mL) in THF and stirred at room temperature for 3 h. The reaction mixture was then evaporated to dryness and applied on a column of silica gel equilibrated and eluted with ethyl acetate-hexane (1:1). Yield of the syrupy product was 340 mg.

The 340 mg of product obtained was dissolved in DMF (10 mL) and then reacted with sulfuryl chloride (255 mL) in the presence of imidazole (741 mg) followed by reaction with sodium azide (500 mg) as described in Step 3A. After purification, the product was obtained as a syrup (227 mg). $^1$H NMR (CDCl$_3$) d: 8.08 (m, 2H), 7.57 (m, 1H), 7.45 (m, 2H) (o, m, and para hydrogens of 6-O-benzoate), 4.49 (m, 1H, H-5), 4.46 (dd, 1H, H-6a, $J_{6a,5}$=3.2 Hz, $J_{6a,b}$=12.0 Hz), 4.35 (dd, 1H, H-6b, $J_{6b,5}$=6.1 Hz), 3.41 and 3.35 (distorted doublets, 2H, H-1a,b), 3.29 (s, 3H, OMe), 2.13 (m, 4H, hydrogens at C-3 and C-4).

Step 4: 1-N-(1-Azido-6-O-benzoyl-1,3,4-trideoxy-D-glycero-β-D-hex-2-ulofuranosyl) thymine The azido glycoside from Step 3A (350 mg) and 2,4-di-O-trimethylsilylthymine (620 mL) were coupled in a mixture of 2:1 nitromethane-dichloromethane (15 mL) using trimethylsilyl triflate as described in Step 9, Example 1. Final purification by HPLC afforded the desired product and the αanomer. Yield β=52 mg. α=107 mg. Hydrolysed product=102 mg. $^1$H NMR (β anomer, CDCl$_3$) d: 9.1 (broad s, 1H, N$_3$-H), 7.96, 7.57, 7.43 (m, 5H, 6'-O-benzoate hydrogens), 7.71 (quartet, 1H, H-6), 4.69 (m, 1H, H-5'), 4.62 (dd, 1H, H-6'a, J=3.3, 12.4 Hz), 4.41 (dd, 1H, H-6'b, J=4.8, 12.4 Hz), 3.74 and 3.62 (2×d, 2H, H-1'a,b, J=12.8 Hz), 2.96 (m, 1H, H-3β, J=4.8, 8.0, 14.5 Hz), 2.50 (m, 1H, H-3'a, J=8.0, 9.2, 14.5 Hz), 2.21 (m, 1H, H-4'a), 1.99 (m, 1H, H$_4$'β), 1.68 (d, 3H, C-5 methyl group).

α Anomer (CDCl$_3$) d: 9.24 (broad s, 1H, N$_3$-H), 8.08, 7.60, 7.47 (m, 5H, 6'-O-benzoate hydrogens), 7.55 (m, 1H, H-6), 4.60 to 4.40 (m, 3H, H-5', H-6'a,b), 3.80 and 3.70 (2×d, 2H, H-1'a,b, J=12.9 Hz), 2.77 (m, 1H, H-3'a, J=5.8, 6.9, 14.4 Hz), 2.54 (m, 1H, H-3'β, J=6.8, 8.0, 14.4 Hz), 2.06 (m, 2H, H-4'α and β), 1.93 (d, 3H, C-5 methyl group).

Step 5A: 1-N-(1-Azido-1,3,4-trideoxy-D-glycero-β-D-hex-2-ulofuranosyl) thymine De-O-benzoylation of the α-anomer obtained in Step 4 (52 mg) with sodium methoxide in methanol afforded the product as a colorless solid (37 mg). $^1$H NMR (D$_2$O) d: 8.04 (quartet, 1H, H-5), 4.34 (m, 1H, H-5'), 3.80 (d, 1H, H-1'a, J=13.0 Hz), 3.75 (dd, 1H, H-6'a, J=3.4, 12.4 Hz), 3.59 (d, 1H, H-1'b), 3.58 (dd, 1H, H-6'b, J=5.5, 12.4 Hz), 2.76 (m, 1H, H-3'β, J=4.1, 7.8, 14.5 Hz), 2.32 (m, 1H, H-3'a, J=8.3, 10.3, 14.5 Hz), 1.99 (m, 1H, H-4'a), 1.87 (d, 3H, C-5 Me), 1.79 (m, 1H, H-4'β).

Step 5B: 1-N-(1-Azido-1,3,4-trideoxy-D-glycero-α-D-hex-2-ulofuranosyl) thymine The αanomer was prepared as described in Step 5A from the β-anomer of Step 4.

α Anomer (D$_2$O) d: 7.76 (broad d, 1H, H-5), 4.23 (m, 1H, H-5'), 3.81 (d, 1H, H-1'a, J=13.3 Hz), 3.71 (dd, 1H, H-6'a, J=4.0, 11.8 Hz), 3.63 (dd, 1H, H-6'b, J=5.9, 11.8 Hz), 3.58 (d, 1H, H-1'b), 2.58 (m, 1H, H-3'a, J=7.4, 14.4 Hz), 2.39 (m, 1H, H-3'β, J=5.7, 9.0, 14.4 Hz), 1.93 and 1.81 (m, 2H, H-4'α and β), 1.87 (broad s, 3H, C-5 Me).

EXAMPLE 3

Synthesis of a Compound of Formula I where $R^1$ is H$_4$P$_3$O$_9$, $R^2$ is OR$^3$, $R^3$ is H, B is thymine and A is H; 1-N-(3',4'-Dideoxy-D-glycero-beta-D-hex-2-ulofuranosyl)thymine 6-triphosphate The compound of Example 1, Step 10, 1-N-(3,4-Dideoxy-D-glycero-beta-D-hex-2-ulofuranosyl)thymine (23.3 mg, 90.9 μmol) and cytosine (10.4 mg, 94 μmol) were suspended in trimethyl phosphate (0.20 mL). Phosphorus oxychloride (14 μL, 150 μmol) was added and the mixture was stirred under argon at ambient temperature for 40 minutes. The reaction mixture was added dropwise to a solution of tris(tri-n-butylammonium) pyrophosphate (1.0M in DMF; 1.2 mL). The solution was stirred under argon at ambient temperature for 30 minutes and then added dropwise to a precooled (0° C.) of triethylamine (140 μL) in water (2.0 mL). After standing at 2° C. overnight, the solution was stripped down, taken up in water (10 mL) and applied to a column (1×30 cm bed) of DEAE-Sephadex A-25-120 that had been pre-equilibrated with pH 7.6 aqueous triethylammonium bicarbonate (TEAB) (1.0→0.1M). The column was eluted with a linear gradient of TEAB [0.1M (150 mL)→1.0M (150 mL)]. The elution was monitored by absorbance at 270 nm. The fractions corresponding to the major peak eluting at roughly 0.6M were pooled, stripped, and co-evaporated with ethanol (2×). The yield was 9.8 μmol (11%) (assuming an absorption coefficient of 9,600 at 267.5 nm (max)) of the triethylammonium salt. HPLC (Zorbax SAX, 0.2M pH 6.5 aqueous potassium phosphate) showed the material to be roughly 85% pure. The major component showed: $^{31}$P NMR (D$_2$O) −21.82 (b, beta-P), −9.90 (d, 20 hz, alpha-P), −9.02 (b, gamma-P); 1H NMR (D$_2$O): ppm 1.7−1.9 and 2.20−2.35 (m's, H-3'a,3'b,4'a,4'b), 1.91 (s, 5-CH$_3$), 3.76 (d, 12 hz, H-1'a), 3.99 (d, 12 hz, H-1'b), 3.99 (m, H-6'a), 4.18 (m, H-6'b), 4.52 (m, H-5'), and 8.02 (s, H-6).

EXAMPLE 4

Synthesis of a Compound of Formula I where R$^1$ is H$_4$P$_3$O$_9$, R$^2$ is N$_3$, B is thymine and A is H; 1-N-(1-azido-1,3,4-trideoxy-D-glycero-beta-D-hex-2-ulofuranosyl)thymine 6'-triphosphate The compound of Example 2, 1-N-(1-azido-1,3,4-trideoxy-D-glycero-beta-D-hex-2-ulofuranosyl)thymine (37 mg, 132 μmol) and cytosine (13.7 mg, 123 μmol) were suspended in trimethyl phosphate (0.30 mL). Phosphorus oxychloride (28 μL, 300 μmol) was added and the mixture was stirred under argon at ambient temperature for 30 minutes. The reaction mixture was added dropwise to a solution of tris(tri-n-butylammonium) pyrophosphate (1.0M in DMF; 0.9 mL). The solution was stirred under argon at ambient temperature for 5 minutes and then added dropwise to a precooled (0° C.) of triethylamine (210 μL) in water (3.0 mL). After standing at 2° C. overnight, the solution was stripped down, taken up in water (15 mL) and applied to a column (1×30 cm bed) of DEAE-Sephadex A-25-120 that had been pre-equilibrated with pH 7.6 aqueous triethylammonium bicarbonate (TEAB) (1.0→0.1M). The column was eluted with a linear gradient of TEAB [0.1M (150 mL)→1.0M (150 mL)]. The elution was monitored by absorbance at 270 nm. The fractions corresponding to the major peak eluting at roughly 0.5M were pooled, stripped, and co-evaporated with ethanol (2×). The yield was 59 μmol (45%) (assuming an absorption coefficient of 10,000 at 270 nm (max)) of the triethylammonium salt. HPLC (Zorbax SAX, 0.2M pH 6.5 aqueous potassium phosphate) showed the material to be 99% pure. $^{31}$P NMR (D$_2$O): ppm −21.06 (t, 20 hz, beta-P), −9.80 (d, 20 hz, alpha-P), -4.0 (d, 21 hz, gamma-P).

EXAMPLE 5

Synthesis of a Compound of Formula I where R$^1$ is H$_4$P$_3$O$_9$, R$^2$ is NH$_2$, B is thymine and A is H; 1-N-(1-amino-1,3,4-trideoxy-D-glycero-beta-D-hex-2-ulofuranosyl)thymine 6'-triphosphate 1-N-(1-azido-1,3,4-trideoxy-D-glycero-beta-D-hex-2-ulofuranosyl) thimine triphosphate (20 μmol) was dissolved in water (1 mL) and 10% palladium on carbon (2 mg) was added. The reaction mixture was stirred under a hydrogen atmosphere for 75 minutes. The catalyst was removed by filtration and 1.0M pH 7.6 aq. TEAB (100 μL) was added. The solution was applied to a column (1×30 cm bed) of DEAE-Sephadex A-25-120 that had been preequilibrated with pH 7.6 aqueous triethylammonium bicarbonate (TEAB) (1.0→0.1M). the column was eluted with a linear gradient of TEAB [0.1M (150 mL)→1.0M (150 mL)]. The elution was monitored by absorbance at 270 nm. The fractions corresponding to the major peak were pooled, stripped, and co-evaporated with ethanol (2×). The yield was 12.8 μmol (64%) (assuming an absorption coefficient of 10,000 at 268.5 nm (max)) of the triethylammonium salt. HPLC (Zorbax SAX, 0.2M pH 6.5 aqueous potassium phosphate) showed the material to be >98% pure.

EXAMPLE 6

Synthesis of a Compound of Formula I where R$^1$ is H$_4$P$_3$O$_9$, R$^2$ is NHBiotin, B is thymine and A is H; 1-N-(1-(6-biotinamido)hexanoamido)-1,3,4-trideoxy-D-glycerobeta-D-hex-2-ulofuranosyl)thymine 6'-triphosphate 1-N-(1-amino-1,3,4-trideoxy-D-glycero-beta-D-hex-2-ulofuranosyl)thymine triphosphate (20 μmol) was dissolved in 1.0M pH 7.6 aq. TEAB (100 μL) and sulfosuccinimidyl 6-(Biotinamido)hexanoate sodium salt (5.2 mg, 9 μmol) was added. After standing at 50° C. for 2 hours, the solution was diluted to 1 ml with water and applied to a column (1×19 cm bed) of DEAE-Sephadex A-25-120 that had been pre-equilibrated with pH 7.6 aqueous triethylammonium bicarbonate (TEAB) (1.0→0.1M). the column was eluted with a linear gradient of TEAB [0.1M (150 mL)→1.0M (150 mL)]. The elution was monitored by absorbance at 270 nm. The fractions corresponding to the first product peak (after the large N-hydroxy sulfosuccinimide peak) were pooled, stripped, and co-evaporated with ethanol (2×). The yield was 1.3 μmol (26%) (assuming an absorption coefficient of 10,000 at 272 nm (max)) of the triethylammonium salt. HPLC (C-18, 0→30% acetonitrile in 0.1M TEAA) showed a single peak.

EXAMPLE 7

Synthesis of a compound of Formula I where R$^1$ is H, R$^2$ is N$_3$, B is thymine and A is OH; 1-N-(1-azido-1,3-dideoxy-D-erythro-β-D-hex-2-ulofuranosyl)thymine

Step 1: Methyl 1.3-O-benzylidene-4,6-di-O-benzoyl-α-D-fructofuranoside

A solution of the product from Step 2 of Example 1 (21.0 g) in dichloromethane (500 mL) containing pyridine (18.0 mL) was cooled and benzoyl chloride (21.5 mL) was added in drops. After the addition was over, catalytic amount (about 10 mg) of 4-N,N-dimethylaminopyridine was added and the reaction mixture was stirred at room temperature under nitrogen atmosphere for 20 h. The reaction mixture was washed with 1M ice cold hydrochloric acid (till the aqueous layer was acidic), water and saturated sodium bicarbonate solution. Evaporation of the solvent gave a syrup. Purification of this on a column of Silica Gel using ethyl acetate - hexane (1:5) as eluant gave a homogeneous product (23.5 g).

Step 2: Methyl 4.6-di-O-benzoyl-1-O-(t-butyl dimethyl)silyl-α,β-D-fructofuranoside The product from step 1 (23.5 g) was dissolved in anhydrous methanol containing p-toluenesulfonic acid (827 mg) and refluxed under nitrogen for 1 h. The solution was cooled and neutralized with triethyl amine and the solution was evaporated to dryness to obtain a syrup (25.0 g). This syrup was dissolved in 100 mL of DMF and evaporated before proceeding to the next step. This ensured the removal of traces of methanol from the product.

A portion of the above syrup (5.0 g) was dissolved in anhydrous DMF (100 mL) and cooled to 0° C. Imidazole (1.0 g) and t-butylbimethylsilyl chloride (2.2 g) were added and the solution was stirred for 3 h. at room temperature. The reaction mixture was again cooled and additional portions of imidazole (1.0 g) and t-butyldimethylsilyl chloride were added. After 20 h. at room temperature, the reaction was evidenced to be complete. The reaction mixture was evaporated to dryness and the residue was extracted with dichloromethane. This was then washed with water, ice cold 1M hydrochloric acid and saturated sodium bicarbonate solution. Finally, the organic layer was dried over anhydrous magnesium sulfate, filtered and the solvent was evaporated to obtain a syrup containing two products. These were separated by chromatography on a column of Silica Gel using ethyl acetate-hexane (1:6) as eluant. The less polar material (2.54 g) was identified by 1H NMR as the α anomer and the second product (2.11 g) was the corresponding β anomer.

1H NMR of β-anomer (CDCl3) δ: 8.08, 7.57 and 7.42 (m, benzoate hydrogens), 5.32 (dd, 1H, H-4), 4.71 (dd, H-6a), 4.59 (dd, 1H, H-6b), 4.43 (m, 2H, H-5 and H-3), 3.98 (d, 1H, H-1a), 3.84 (d, 1H, H-1$_b$), 3.59 (d, 1H, OH), 3.35 (s, 3H, OCH3).

1H NMR of β-anomer (CDCl3) δ: 8.07, 7.58 and 7.45 (m, benzoate hydrogens), 5.55 (t, 1H, H-4), 4.68 (dd, 1H, H-6a), 4.58 (m, 1H, H-3), 4.52 (dd, 1H, H-6b), 4.38 (m, 1H, H-5), 3.8 (dd, 2H, H-1a and H-1$_b$), 3.38 (s, 3H, OCH3). 13C NMR (CDCl3) δ: 166.3, 166.2, 133.4, 133.0, 129.8, 129.7, 128.4, 128.3, 104.5, 80.0, 78.6, 77.0, 65.2, 61.5, 49.4, 25.8, 18.3, −5.4, −5.5.

Step 3a: Methyl 3-deoxy-4,6-di-O-benzoyl-1-O-(t-butyl dimethyl)silyl-α-D-fructofuranoside The α-anomer from Step 2 (2.54 g) was dissolved in 1,2-dichloroethane (50 mL) containing thiocarbonyl-diimidazole (12.0 g) and refluxed under nitrogen for 4 days. The reaction mixture was worked as described in step 4 of Example 1. The product was converted to the title compound by reaction with tri-n-butyl tin hydride (3.5 mL) in toluene as described in step 4 of Example 1. The product was purified by chromatography on a column of Silica Gel using ethyl acetate - hexane (1:18) as eluant to obtain 1.3 g of a syrup. 1H NMR (CDCl3) δ: 8.06, 7.58 and 7.44 (m, benzoate hydrogens), 5.48 (m, 1H, H-4), 4.63−4.48 (m, 3H, H-6a, H-6b, H-5), 3.79 (d, 1H, H-1a), 3.61 (d, 1H, H-1$_b$), 3.48 (s, 3H, OCH3), 2.69 (dd, 1H, H-3a), 2.26 (dd, 1H, H-3b). 13C NMR: 166.2, 166.1, 133.3, 133.0, 129.8, 129.7, 128.4, 128.3, 108.2, 81.9, 81.0, 79.8, 64.4, 61.0, 48.7, 25.7, 18.1, −5.5, −5.6.

Step 3b: Methyl 3-deoxy-4,6-di-O-benzoyl-1-O-(t-butyl dimethyl)silyl-β-D-fructofuranoside This was prepared from 2.11 g of the β anomer of Step 2 as described in Step 3a. The weight of the product was 1.21 g. 1H NMR (CDCl3) δ: 8.06, 7.57 and 7.44 (m, benzoate hydrogens), 5.61 (m, 1H, H-4), 4.65−4.48 (m, 3H, H-6a and H-6b, H-5), 3.7 (d, 1H, H-1a), 3.61 (d, 1H, H-1$_b$), 3.31 (s, 3H, OCH3), 2.65 (dd, 1H, H-3a), 2.48(dd, 1H, H-3b).

Step 4a: Methyl 1-azido-1.3-dideoxy-4.6-di-O-benzoyl-α-D-fructofuranoside

The product from Step 3a (1.9 g) was dissolved in THF (100 mL). Tetrabutyl-ammonium fluoride solution (1 M) in THF (4.75 mL) was added and the reaction mixture was stirred at room temperature for 20 min. The reaction mixture was evaporated to dryness and the residue was dissolved in dichloromethane. This was then washed with water, ice cold 0.5M hydrochloric acid, water and saturated sodium chloride sloution. Evaporation of the solvent gave a syrup (2.15 g) which was redissolved in anhydrous DMF (50 mL) and cooled to −20° C. Sulfuryl chloride (0.9 mL) and imidazole 0.75 g) were added and the reaction was gently warmed up to room temperature with stirring. After 1 h., the solvent was evaporated to dryness and the residue was dissolved in dichloromethane. The solution was washed with water, ice cold 1M hydrochloric acid and saturated sodium bicarbonate solution. Evaporation of the solvent gave a syrup which was dissolved in anhydrous DMF (50 mL) containing sodium azide (1.0 g). After stirring at 50° C. for 24 h., the solvent was evaporated to dryness and the residue was dissolved in dichloromethane. The solution was washed with water, ice cold 1M hydrochloric acid and saturated sodium bicarbonate solution. Evaporation of the solvent gave a syrup which was purified by chromatography on a column of Silica Gel using ethyl acetate-hexane (1:10) as eluant. The structure of the product (1.08 g) was confirmed by 1H NMR. 1H NMR (CDCl3) δ: 8.08, 7.6, and 7.47 (m, benzoate hydrogens), 5.54 (m, 1H, H-4), 4.53− 4.70 (m, 3H, H-6a and H-6b, H-5), 3.42 (dd, 2H, H-1a and H-1$_b$), 3.4 (s, 3H, OCH3), 2.67 (dd, 1H, H-3a), 2.34 (dd, 1H, H-3b).

Step 4b: Methyl 1-azido-1,3-dideoxy-4,6-di-O-benzoyl-β-D-fructofuranoside

The product from step 3b (500 mg) was converted to compound (258 mg) as described in step 4a. 1H NMR (CDCl3) δ: 8.07, 7.60, 7.46 (m, benzoate hydrogens), 5.66 (m, 1H, H-4), 4.63 (m, 2H, H-5 and H-6a), 4.53 (dd, 1H, H-6b), 3.49 (dd, 2H, H-1a and H-1$_b$), 3.33 (s, 3H, OCH3), 2.72 (dd, 1H, H-3a), 2.46 (dd, 1H, H-3b).

Step 5: 1-N-(1-azido-3,6-dibenzoyl)-1,3-dideoxy-D-erytho-β-D-hex-2-ulo(furanosyl)thymine The product of Step 4b is converted to the product of Step 5 using the method and reagents described in Step 4 of Example 2.

Step 6: 1-N-(1-azido-1,3-dideoxy-D-erythro-β-D-hex-ulofuranosyl)thymine

The product of Step 5 is converted to the title compound by reaction with sodium methoxide in methanol as described in Step 10 of Example 1.

EXAMPLE 8

This example demonstrates a method of use of the compound of Example 6 (which is a compound of Formula I where $R^1$ is $H_4P_3O_9$, $R^2$ is NHBiotin, B is thymine and A is H; 1-N-(1'-(6-biotinamido)hexanoamido)-1,3,4-trideoxy-D-glycero-beta-D-hex-2-ulofuranosyl}thymine 6'-triphosphate as a terminator in a Taq Polymerase DNA chain extension reaction.

A reaction mixture was prepared containing 12 ul M13mpDNA at 0.25 uG/ul (New England Biolabs), 3 ul SF 505 labeled universal primer at 0.0001 OD/ul, 3 ul Taq 10×buffer (166 mM ammonium sulfate, 670 mM Tris pH 8.8, 67 mM $MgCl_2$, 100 mM beta-mercaptoethanol, 67 uM EDTA, 1700 uG/ml Bovine Serum Albumin; New England Biolabs) and 5 ul $dh_2O$. This was boiled for 2 minutes and then 5 ul of an Extension Mixture (prepared from: dATP, 250 uM; dCTP, 250 uM; dGTP 250 ul; dGTP, 250 ul; dTTP, 25 uM; and the product of Example 6, 500 uM) and 1 ul Taq polymerase (Cetus, Emeryville, Calif.) were added. This was mixed and then incubated at 70° C. for 30 minutes. The reaction mixture was then passed through a pre-washed G-50 spin column and then dried in a Speed-Vac for 45 minutes. The residue was suspended in 5 ul of formamide and heated at 68° C. for 5 minutes. 3 ul of this was loaded onto a Genesis 2000 DNA Analysis System (Du Pont) and electophoresed for 8 hours. The result of the electrophoresis was compared with that of a control experiment in which an identical reaction was carried out except that 2',3'-dideoxy-b-D-glyceropentofuranosylthymine, a natural terminator, was used in place of the product of Example 6. The comparison showed that a similar distribution of extension products was obtained using either the natural terminator or the compound of Example 6 as the chain terminator. This example demonstrates the utility of compounds of Formula I as substrates in extension reactions using DNA polymerase from thermus aquaticus (Taq Polymerase).

We claim:

1. A compound of Formula I

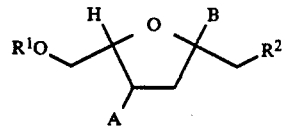

wherein:
   $R^1$ is $H_2PO_3$, $H_3P_2O_6$, $H_4P_3O_9$ or the salts thereof, or H;
   B is a naturally occurring nucleic acid base or either the synthetically modified nucleic acid base; inosine or a deazaadenosine;
   $R^2$ is $OR^3$, $N_3$, Y-Biotinoyl, or $NHC=O(CH_2)_n$Y-Biotinoyl; wherein:
   $R^3$ is H, alkyl containing 1 to 5 carbon atoms, benzyl, acyl containing 1 to 5 carbon atoms, or aroyl wherein the aryl group of the aroyl is benzene or a benzene substituted with at least one alkyl group ($C_1$–$C_4$), one halogen atom, or one methoxy group;
   Y is NH or O;
   n is 1–10; and
   A is H or OH; provided that when A is OH, $R^1$ and $R^3$ cannot both be H.

2. The compound as recited in claim 1 wherein:
   $R^1$ is $H_2PO_3$, $H_3P_2O_6$, $H_4P_3O_9$ or the salts thereof, or H;
   B is a naturally occurring nucleic acid base;
   $R^2$ is OH, $N_3$, or Y-Biotinoyl; and
   A is H.

3. The compound as recited in claim 1 wherein:
   $R^1$ is $H_4P_3O_9$;
   B is thymine;
   $R^2$ is OH, $N_3$, or Y-Biotinoyl; and
   A is H.

* * * * *